(12) United States Patent
Ahn et al.

(10) Patent No.: US 12,656,262 B2
(45) Date of Patent: Jun. 16, 2026

(54) COLOR GAS SENSOR MODULE COMPRISING OPTICAL MEASUREMENT DEVICE

(71) Applicant: SEOUL NATIONAL UNIVERSITY R&DB FOUNDATION, Seoul (KR)

(72) Inventors: Sung Hoon Ahn, Seongnam-si (KR); Young Gyun Kim, Suwon-si (KR)

(73) Assignee: SEOUL NATIONAL UNIVERSITY R&DB FOUNDATION, Seoul (KR)

( * ) Notice: Subject to any disclaimer, the term of this patent is extended or adjusted under 35 U.S.C. 154(b) by 263 days.

(21) Appl. No.: 18/564,226

(22) PCT Filed: May 27, 2021

(86) PCT No.: PCT/KR2021/006572
§ 371 (c)(1),
(2) Date: Jan. 16, 2024

(87) PCT Pub. No.: WO2022/250178
PCT Pub. Date: Dec. 1, 2022

(65) Prior Publication Data
US 2024/0272084 A1 Aug. 15, 2024

(30) Foreign Application Priority Data

May 26, 2021 (KR) ........................ 10-2021-0067911

(51) Int. Cl.
*G01N 21/78* (2006.01)
*G01N 1/22* (2006.01)
(Continued)

(52) U.S. Cl.
CPC ......... *G01N 21/783* (2013.01); *G01N 1/2205* (2013.01); *G01N 21/05* (2013.01);
(Continued)

(58) Field of Classification Search
CPC .... G01N 21/783; G01N 1/2205; G01N 21/05; G01N 21/552; G01N 33/00;
(Continued)

(56) References Cited

U.S. PATENT DOCUMENTS 10,996,174 B2 * 5/2021 Nakamura ......... G01N 33/0027
2011/0181879 A1 7/2011 Chen et al.
(Continued)

FOREIGN PATENT DOCUMENTS

JP 2019-196957 A 11/2019
KR 10-2012-0070160 A 6/2012
(Continued)

OTHER PUBLICATIONS

Serhatlioglu, Murat, et al. "Perfectly absorbing ultra thin interference coatings for hydrogen sensing." Optics Letters 41.8 (2016):1724-1727 (Year: 2016).*
(Continued)

*Primary Examiner* — Dominic J Bologna
(74) *Attorney, Agent, or Firm* — Kilpatrick Townsend & Stockton LLP

(57) ABSTRACT

The present disclosure relates to a color gas sensor module including an optical measurement device, a housing having an interior space therein and a gas movement passage allowing a gas to move from outside to the interior space, wherein the optical measurement device is provided in the housing and includes a light emitter that emit light and a light receiver that receives reflected light, and a gas sensor included in the housing and changing color by reacting with gas, wherein the light emitter emits light to the gas sensor, and the light receiver receives light reflected from the gas sensor.

13 Claims, 9 Drawing Sheets

(51) Int. Cl.

| | |
|---|---|
| *G01N 21/03* | (2006.01) |
| *G01N 21/05* | (2006.01) |
| *G01N 21/552* | (2014.01) |
| *G01N 21/77* | (2006.01) |
| *G01N 33/00* | (2006.01) |

(52) U.S. Cl.
CPC .......... *G01N 21/552* (2013.01); *G01N 33/00* (2013.01); *G01N 33/0027* (2013.01); *G01N 1/2273* (2013.01); *G01N 21/031* (2013.01); *G01N 2021/7773* (2013.01)

(58) Field of Classification Search
CPC ............. G01N 33/0027; G01N 1/2273; G01N 21/031; G01N 2021/7773
See application file for complete search history.

(56) References Cited

U.S. PATENT DOCUMENTS

| | | | |
|---|---|---|---|
| 2014/0186215 A1 | 7/2014 | Shinta et al. | |
| 2016/0327533 A1* | 11/2016 | Jin | G01N 21/78 |
| 2017/0045486 A1* | 2/2017 | Wan | G01N 21/554 |
| 2017/0089832 A1* | 3/2017 | Uemura | G01N 21/783 |
| 2019/0064060 A1 | 2/2019 | Gudeman et al. | |
| 2020/0400604 A1* | 12/2020 | Jung | G01N 27/227 |
| 2021/0030290 A1 | 2/2021 | Lee et al. | |
| 2021/0310906 A1* | 10/2021 | Takeuchi | B01J 20/22 |

FOREIGN PATENT DOCUMENTS

| | | |
|---|---|---|
| KR | 10-2014-0031314 A | 3/2014 |
| KR | 10-2018-0021691 A | 3/2018 |
| KR | 10-2019-0020203 A | 2/2019 |
| KR | 10-2019-0094562 A | 8/2019 |
| KR | 10-2176119 B1 | 11/2020 |
| WO | 2016/179067 A1 | 11/2016 |

OTHER PUBLICATIONS

KR Intellectual Property Office, Request for the Submission of an Opinion; Application No. 10-2021-0067911; Dated Feb. 10, 2023; 12 pgs.
KR Intellectual Property Office; Written Decision on Registration; Application No. 10-2021-0067911; Dated Jun. 26, 2023; 9 pgs.
Serhatlioglu et al.; Perfectly Absorbing Ultra Thin Interference Coatings for Hydrogen Sensing; Optics Letters; vol. 41, No. 8, Apr. 15, 2016; 4 pgs.
Li et al.; Humidity Sensor With a PVA-Coated Photonic Crystal Fiber Interferometer; IEEE Sensors Journal, vol. 13, No. 6; Jun. 2013; 3 pgs.
Duan et al.; Dynamic Plasmonic Colour Display; Nature Communications; Article Received Jun. 23, 2016; Accepted Jan. 12, 2017; Published Feb. 24, 2017; DOI: 10.1038/ncomms14606; 9 pgs.
Yu et al., Colorimetric Ethanol Indicator Based on Instantaneous, Localized Wetting of a Photonic Crystal; ACS Applied Materials & Interfaces 2020, 12, 1924-1929; 6 pgs.
Hedayati et al.; Review of Metasurface Plasmonic Structural Color; Plasmonics (2017) 12:1463-1479; DOI 10.1007/s11468-016-0407-y; CrossMark; Received May 9, 2016; Accepted Oct. 3, 2016; Published online Oct. 20, 2016; Springer Science+Business Media New York 2016; 17 pgs.
Jaehyuck Jang et al., "Self-Powered Humidity Sensor Using Chitosan-Based Plasmonic Metal- Hydrogel-Metal Filters," Advanced Optical Materials, 2020, 8, 1901932, DOI: 10.1002/adom.201901932, www.advopticalmat.de 7 pages.

* cited by examiner (a)

(b)

(a)

(b)

(a)

(b)

COLOR GAS SENSOR MODULE COMPRISING OPTICAL MEASUREMENT DEVICE

TECHNICAL FIELD

The present disclosure relates to a color gas sensor module including an optical measurement device, and more particularly, to a color gas sensor module including an optical measurement device for quantitatively measuring a sensor indicating a color change in response to detecting gas through a module having a gas sensor that changes color in response to a gas, and an optical measurement device including a light emitter for emitting light to a gas sensor and a light receiver for receiving the light reflected from the gas sensor.

BACKGROUND ART

A gas sensor is used for sensing gas. Most conventional gas sensors include a semiconductor device and have a MOFSET structure. A conventional gas sensor operates as described below. A conventional gas operation method is as follows. The conventional gas sensor includes a material circuit and an additional heating device is passed through the material circuit. When a gas passes through the conventional gas sensor, the material circuit part is doped, a resistance value of the circuit changes, and this change is amplified via MOFSET structure to measure the gas.

Conventional gas sensors have the advantage of high sensitivity, but they also have the disadvantage of requiring separate heating devices and separate measuring equipment to measure a current flowing through the material circuit in the device. In general industries, it may be necessary to measure gas accurately, but in some cases, gas may be simply measured.

Recently, as applications for using gas sensors at low power have gradually increased, and especially in the markets of mobile devices, research on wearable devices and electronic devices including gas sensors operating at low power has been conducted.

However, since conventional gas sensors can be recognized only by using a data processing device and a separate display device while using a separate heating device that require high power, it is difficult to include such conventional gas sensors in mobile devices or electronic devices.

Further, as miniaturization of conventional gas sensors to be installed in mobile devices, wearable devices, and other electronic devices is difficult, other problems such as the possibility of measuring only a current gas concentration through a conventional gas sensor and equipping a gas sensor with a separate circuit in order to measure gas in a cumulative manner have occurred. In addition, the conventional gas sensors are vulnerable to humidity and temperature factors, and thus, their durability is weak when exposed to an external environment.

DISCLOSURE

Technical Problem

The present disclosure is to solve the above problems, and more specifically relates to a color gas sensor module including an optical measurement device for quantitatively measuring a sensor indicating a color change in response to detecting gas through a module having a gas sensor that changes color in response to a gas, and an optical measurement device including a light emitter for emitting light to the gas sensor and a light receiver for receiving the light reflected from the gas sensor.

Technical Solution

A color gas sensor module including an optical measurement device of the present disclosure for solving the above-described problem is equipped with a sensor for sensing gas and includes a housing having an interior space therein and a gas movement passage allowing a gas to move from outside to the interior space, the optical measurement device provided in the housing and including a light emitter for emitting light and a light receiver for receiving reflected light, and a gas sensor provided in the housing and configured to change color by reacting with the gas, wherein the light emitter emits light to the gas sensor and the light receiver receives the light reflected from the gas sensor.

In a color gas sensor module with an optical measurement device of the present disclosure for solving the above-described problems, the light emitter of the optical measurement device may emit light onto the gas sensor, and the light receiver may measure a reflectivity of a wavelength of light reflected from the gas sensor.

In a color gas sensor module with an optical measurement device of the present disclosure for solving the above-described problems, the housing may include a plurality of gas movement passages.

In a color gas sensor module with an optical measurement device of the present disclosure for solving the above-described problems, at least one of the plurality of the gas movement passages may include a membrane capable of selectively removing a designated gas.

In a color gas sensor module with an optical measurement device of the present disclosure for solving the above-described problems, the gas sensor may include two or more film layers and an optical layer between the film layers.

In a color gas sensor module with an optical measurement device of the present disclosure for solving the above-described problems, the film layer of the gas sensor may include a first metal layer including a metal and a second metal layer including a metal, the optical layer may include a first insulator layer having transparency or translucency, and the first insulator layer may be between the first metal layer and the second metal layer.

In a color gas sensor module with an optical measurement device of the present disclosure for solving the above-described problems, the film layer of the gas sensor may further include a third metal layer including a metal, the optical layer may further include a second insulator layer having transparency or translucency, and the second insulator layer may be between the second metal layer and the second metal layer.

In a color gas sensor module with an optical measurement device of the present disclosure for solving the above-described problems, the optical layer of the gas sensor may include a gas reaction metal layer including a metal, and the gas reaction metal layer may react with the gas to become optically transparent or translucent.

In a color gas sensor module with an optical measurement device of the present disclosure for solving the above-described problems, the gas sensor may include a catalyst layer that improves the reactivity to gas when combined with the film layer.

In a color gas sensor module with an optical measurement device of the present disclosure for solving the above-described problems, the film layer of the gas sensor may include an insulator layer, which is optically transparent or translucent.

In a color gas sensor module with an optical measurement device of the present disclosure for solving the above-described problems, the film layer of the gas sensor may include metal layer including a metal material, and an insulator layer having optical transparency or translucency.

In a color gas sensor module with an optical measurement device of the present disclosure for solving the above-described problems, a thickness of the film layer of the gas sensor may change in response to the film layer reacting with gas.

In a color gas sensor module with an optical measurement device of the present disclosure for solving the above-described problems, the gas sensor may include a nano-pattern layer on which patterns are formed, and the nano-pattern layer may change a width between the patterns by reacting with the gas.

In a color gas sensor module with an optical measurement device of the present disclosure for solving the above-described problems, the width between the patterns of the nano-pattern layer may be 200 nm to 3,000 nm.

Advantageous Effects

The present disclosure relates to a color gas sensor module including an optical measurement device, wherein there are such advantages as sensing gas with the use of lower power and presenting the gas in color through a gas sensor reacting with gas to change its color and an optical measurement device, and as making it possible to be miniaturized with the use of low power.

The gas sensor module of the present disclosure has such advantages as making it possible to be mounted to mobile devices, electronic devices and wearable devices for use, as the miniaturization is enabled, while consuming low power.

Also, in the present disclosure, color change of a gas sensor is detected through an optical measurement device to transmit a signal, so that there are such advantages as making it possible to display gas concentration in quantitative way and measure cumulative gas concentration. Additionally, the present disclosure has such advantage as enabling to improve durability, since a membrane is included in a housing equipped with an optical measurement device and a gas sensor.

BEST MODE

Mode for Invention

The present specification clarifies the scope of the present disclosure, explains the principle of the present disclosure, and discloses embodiments so that a person of ordinary skill in the technical field to which the present disclosure belongs may practice the present disclosure. The disclosed embodiments may be implemented in various forms.

Expressions such as "including" or "including" that may be used in various embodiments of the present disclosure refer to the existence of a disclosed function, operation, or component, and do not limit additional one or more functions, operations, or components. In addition, in various embodiments of the present disclosure, terms such as "include" or "have" are intended to specify the existence of features, numbers, steps, actions, components, parts or combinations thereof described in the specification, and should be understood not to preclude the existence or addition of one or more other features or numbers, steps, actions, components, parts or combinations thereof.

When a component is referred to as "connected and coupled" to another component, it should be understood that while the component may be directly connected or coupled to the other component, there may be a new component between the component and the other component. On the other hand, when it is stated that a component is "directly connected" or "directly connected" to another component, it should be understood that there is no new component between the above and the other component.

Terms such as first and second used in the present specification may be used to describe various components, but the components should not be limited by terms. Terms are used only for the purpose of distinguishing one component from another.

The present disclosure relates to a color gas sensor module that includes an optical measurement device that detects gas and displays the concentration of gas in color through a module equipped with an optical measurement device that emits light with a gas sensor that changes color in response to gas. Hereinafter, preferred embodiments of the present disclosure will be described in detail with reference to the accompanying drawings.

A color gas sensor module according to an embodiment of the present disclosure includes a housing 110, an optical measurement device 120, and a gas sensor 200.

Figure 1:
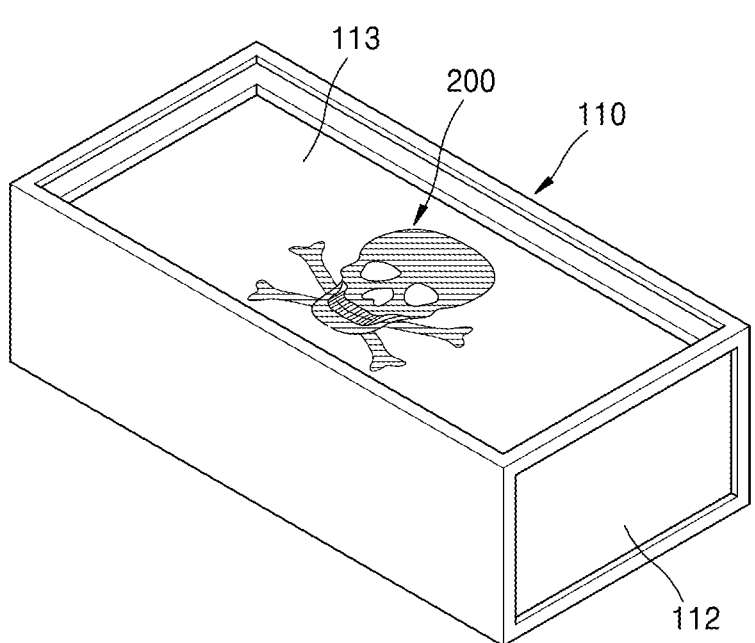
FIG. 1 shows a color gas sensor module including an optical measurement device according to an embodiment of the present disclosure.
Figure 2:
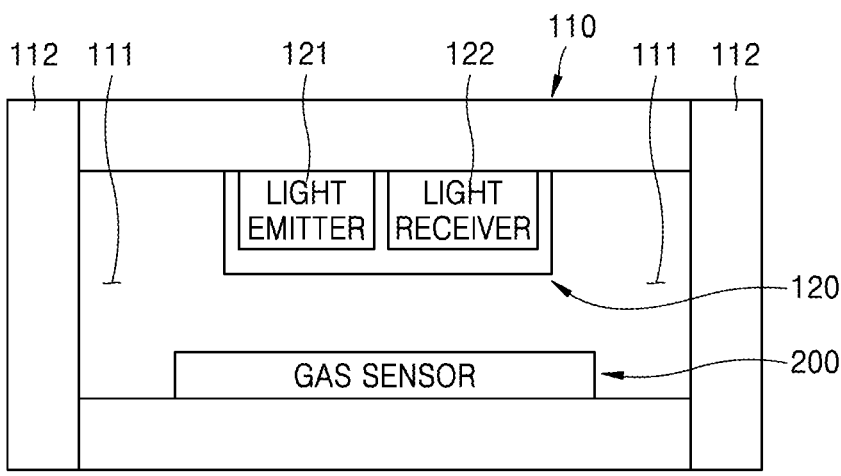
FIG. 2 shows an optical measurement device and a gas sensor inside a housing according to an embodiment of the present disclosure, wherein a membrane is provided in a gas movement passage in the housing.

Referring to FIGS. 1 and 2, the housing 110 has an interior space therein and a gas movement passage 111 through which gas may move from outside to interior.

The gas movement passage 111 is a passage through which gas may enter and exit, and a plurality of the gas movement passages 111 may be provided in the housing 110. Referring to FIG. 2, the housing 110 according to an embodiment of the present disclosure may have a hexahedral shape, and the gas movement passages 111 may be provided at one side and the other side of the housing 110, respectively.

Specifically, the gas movement passages 111 are formed on two sides of the housing 110 as shown in FIG. 1, and top and bottom surfaces of the housing may be closed.

Gas may be introduced into the housing 110 through the gas movement passages 111, and the gas flowing in the housing 110 may react with the gas sensor 200.

Referring FIGS. 1 and 2, at least one of the plurality of the gas movement passages 111 may have a membrane 112 for selectively removing a designated gas.

The membrane 112 may be made of a material selectively removing gases other than gas to be detected. According to an embodiment of the present disclosure, the membrane 112 may be made of a material, such as fluorine-coated fiber material, aluminum anodizing oxide, etc.

However, the present disclosure is not limited to those material, and if any designated gas other than gas to be detected may be selectively removed, the membrane 112 may be made of various materials Referring to FIG. 1, the housing 110 may include a transparent window 113. The transparent window 113 may be made of a transparent or translucent material so as to check the interior space of the housing 110.

Though the transparent window 113, it is possible to check a color change of the gas sensor 200 included in the housing 110 from the outside of the housing 110. The transparent window 113 may be provided on an upper surface of the housing 110, but such is not limited thereto; the transparent window may be installed at various positions, if it is possible to check the interior of the housing 110.

The optical measurement device 120 may be included in the housing 110, and may include a light emitter 121 for emitting light and a light receiver 122 for receiving light reflected. The optical measurement device 120 is included in the housing 110, and after light is emitted from the optical measurement device 120, any color change of the gas sensor 200 may be detected as the optical measurement device 120 receives the reflected light.

More specifically, the light emitter 121 of the optical measurement device 120 may emit the light to the gas sensor 200, and the light receiver 122 may measure reflectivity of a wavelength of the light reflected on the gas sensor 200.

The light emitter 121 may include a monochromic laser having a single center pick, etc., and the light receiver 122 may include a receptor measuring the reflectivity of a specific wavelength. However, the disclosure is not limited to the above description, and the light emitter 121 and the light receiver 122 may have various configurations, if the light emitter 121 can emit light and the light receiver 122 can receive light reflected.

Since the optical measurement device 120 emit light to the gas sensor 200 and the optical measurement device 120 receives light reflected on the gas sensor 200, it may be preferable to place the gas measurement device 120 and the gas sensor 200 at opposite positions.

Specifically, when the gas sensor 200 is placed toward a first direction, the optical measurement device 120 may be placed toward a second direction opposite to the first direction.

The housing 110 or the optical measurement device 120 may include a controller for receiving a signal of the light received in the receiver 122. The controller may receive the signal according to the reflectivity of a wavelength of the reflected light measured in the receiver 122. The controller may determine the color change of the gas sensor 200 through the signal according to the reflectivity of the wavelength measured in the receiver 122.

Specifically, the controller may detect a change in the reflectivity value of wavelength measured in the receiver 122, through which the controller determines the color change of the gas sensor 200.

The controller may determine concentration of gas reacted with the gas sensor 200, accumulated concentration of gas, and etc., through the reflectivity change measured in the receiver 122 or the color change of the gas sensor 200.

The controller may determine accumulated concentration value of the gas, through color change of the gas sensor 200 or reflectivity change measured in the receiver 122, and a current gas concentration value may be determined by differentiating the accumulated concentration value of gas.

The controller may be connected to various mobile device, wearable devices, and electronic devices, and the controller may transmit information about accumulated concentrations of gas, gas concentration, etc., which are determined according to the color change of the gas sensor 200 using the mobile device, the wearable device, the electronic device.

As stated above, the color gas sensor module including the optical measurement device according to the embodiment of the present disclosure has such advantage as dispensing with separate power, because accumulated gas concentration, gas concentration etc., may be measured through a process of changing color in the gas sensor 200.

Further, the controller has the advantage of quantitatively determining the cumulative concentration value of the gas and the concentration value of the gas through the color change value of the gas sensor 200. In addition, since the controller displays the accumulated concentration of gas and the concentration of gas through the color change of the gas sensor 200 without a separate display device, there is an advantage in that the module can be miniaturized.

Additionally, when the color gas sensor module including the optical measurement device according to the embodiment of the present disclosure is mounted to various mobile devices, wearable devices, and electronic devices, it may be possible to display the color change of the gas sensor 200 by reacting with gas through the transparent window or the like.

The gas sensor 200 may be included in the housing 110, and the color changes by reacting with the gas. The gas sensor 200 may be a sensor whose structural color changes by reacting with gas.

According to an embodiment of the present disclosure, the gas sensor 200 may include two or more film layers 210 and an optical layer 220 disposed between the film layers 210. The two film layers 210 of the gas sensor 200 may be mirror layers that reflect light, and the optical layer 220 may be an insulator layer that generates resonance.

Figure 3:
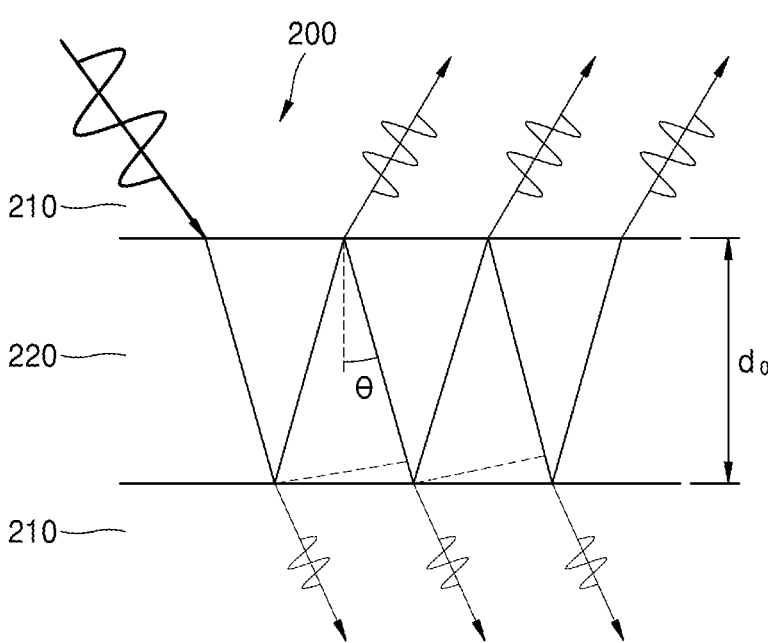
FIG. 3 shows light reflection on a gas sensor including a film layer and an optical layer according to an embodiment of the present disclosure.
Figure 3:
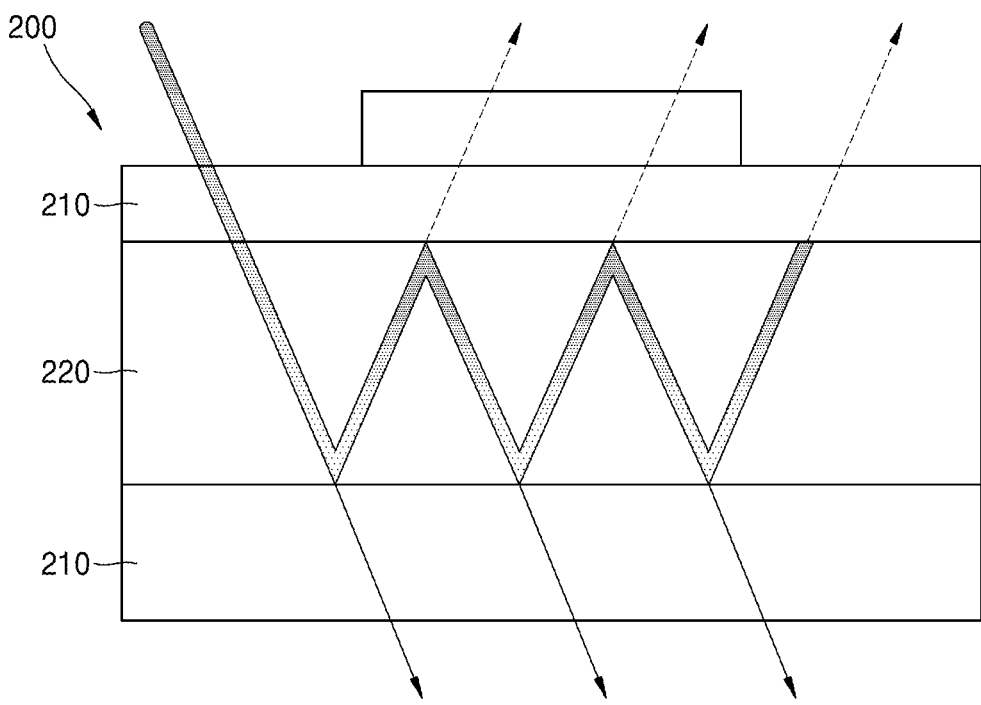

Referring to FIG. 3, when the gas sensor 200 is irradiated with light, the light trapped between the two film layers 210 (two mirror layers) causes resonance in the optical layer 220 (insulator layer), and at the same time, reflective colors may be implemented by selectively absorbing light in a partial wavelength band of the visible light region in the two film layers (two mirror layers).

Figure 4:
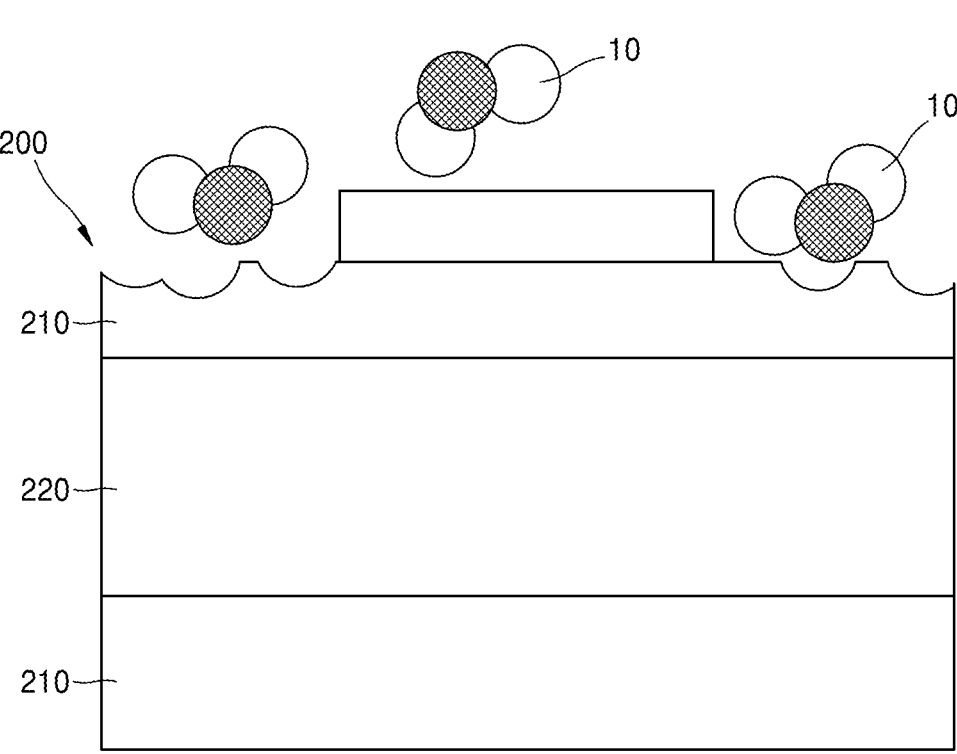
FIG. 4 shows a change of a reflectivity value of light reflected by a gas sensor as a thickness of a film layer changes by a reaction between a gas and a film layer according to an embodiment of the present disclosure.
Figure 4:
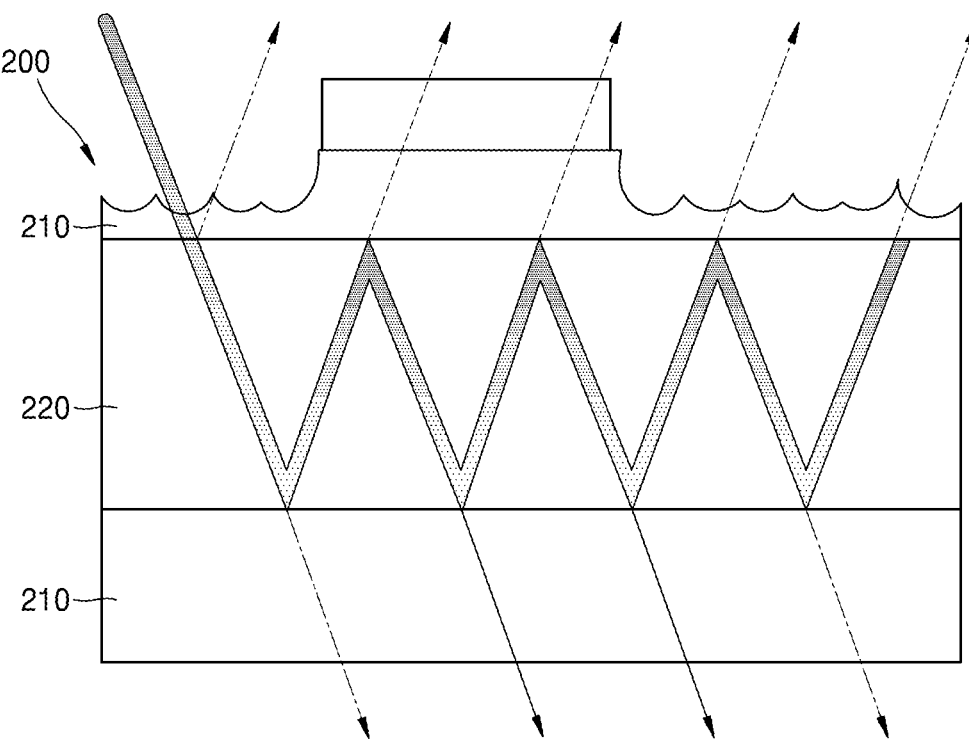

Referring FIG. 4, the film layer 210 of the gas sensor 200 may change the color thereof by reacting with the gas 10.

Here, the film layer 210 that may change the thickness thereof by reacting with the gas 10 may be the film layer 210 included above the gas sensor 200.

When the film layer 210 provided on the upper part of the gas sensor 200 is changed in the thickness by the gas 10, a color change may be implemented as the wavelength band of light absorbed through the gas sensor 200 is changed.

Also, the optical layer 220 may be formed of a material that may change a refractive index by reacting with gas, and as the refractive index of the optical layer 220 changes, a color change may be implemented while a wavelength band of light absorbed by the gas sensor 200 changes.

To this end, the film layer 210 provided on the upper part of the gas sensor 200 may be made of a metal that reacts with gas to change the thickness thereof, and the optical layer 220 may be implemented by a material of which reflective index changes by reacting with gas.

The film layer 210 provided on the gas sensor 200 may be made of a metal that reacts with gas to change the thickness thereof, and the film layer 210 may change the thickness thereof while being corroded by the gas. However, it is not limited to the above, and the film layer 210 may change the thickness thereof due to chemical reaction with other gas other than corrosion.

Figure 5:
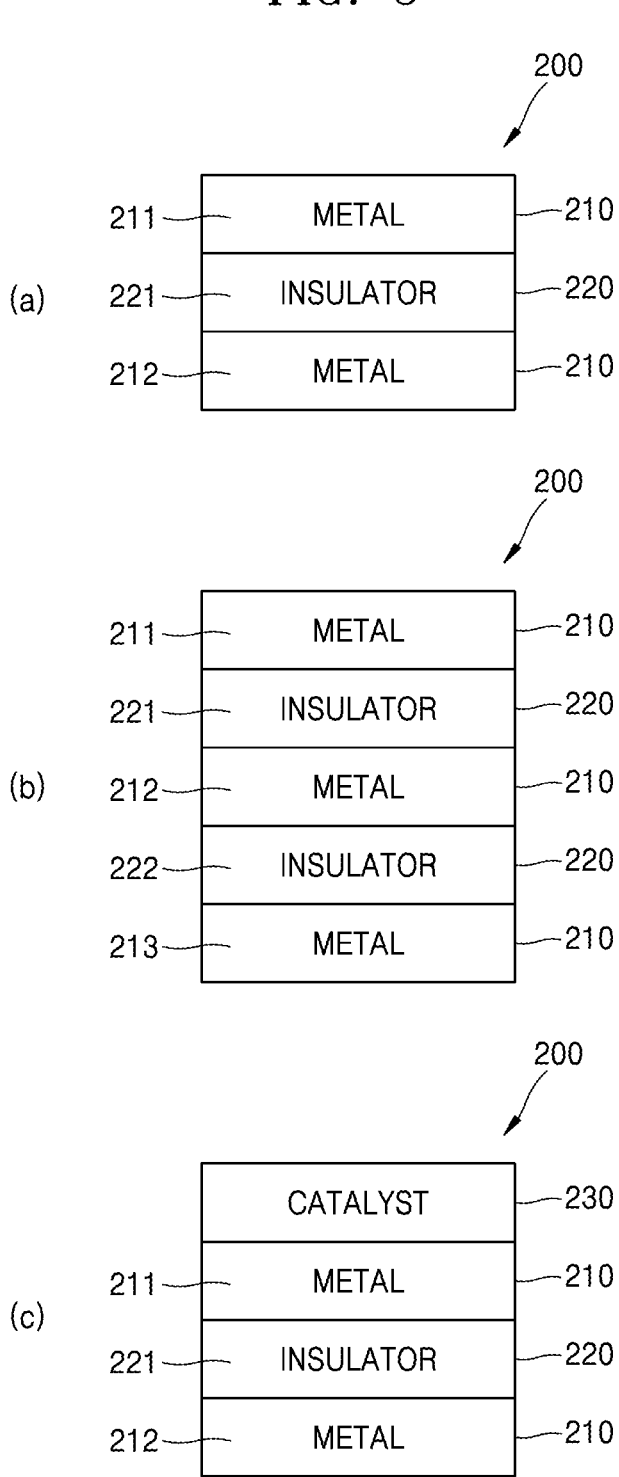
FIGS. 5(*a*) and 5(*b*) show a gas sensor including a metal layer—an insulator layer—a metal layer according to an embodiment of the present disclosure, and FIG. 5(*c*) shows a gas sensor including a catalyst layer.

Referring to FIG. 5(a), the film layer 210 of the gas sensor according to an embodiment of the present disclosure may include a first metal layer 211 made of metal and a second metal layer 212 made of metal, and the optical layer 220 of the gas sensor 200 may include a first insulator layer 221 having transparency or translucency.

The first insulator layer 221 is provided between the first metal layer 211 and the second metal layer 212; the first metal layer 211 and the second metal layer 212 may be a mirror layer and the first insulator layer 221 may be an insulator layer through which light resonates.

In order to let the first mirror layer 211 and the second metal layer 212 serve as a mirror layer, the first metal layer 211 and the second metal layer 212 may be made of a metal that has gloss and reflectivity. Here, the first metal layer 211 may be made of a metal that can be reacted with gas, and the first metal layer 211 may change the thickness thereof by reacting with gas.

The first metal layer 211 and the second metal layer 212 may contain any one of metals selected from Ag, Sn, Ni, Al, Pt and Au, but not limited thereto; various metal may be employed, if gross and reflectivity are given.

In order to let the first insulation layer 221 serve as an insulation layer through which light resonates, the first insulator layer 221 may be optically transparent or translucent. The first insulator layer 221 is made of ceramic or polymer having optically transparent, and the first insulator layer 221 may be made of any one of $SiO_2$, $WO_3$, $TiO_2$, Cr Doped $TiO_2$, $Al_2O_3$, $PO_3$, Hydrogel and Nafion.

Also, the first insulator layer 221 may react with gas to change a refractive index, and the refractive index of the first insulator layer 221 may be changed to implement a color change.

According to an embodiment of the present disclosure, it may be preferable that the first metal layer 211 has a thickness between 5 nm and 50 nm, and it may be preferable that the first insulator layer 221 has the thickness between 10 nm and 1000 nm.

Since humans can recognize light (color) for visible light areas and can use infrared cameras that express color in near-infrared light, it may be preferable that the gas sensor 200 implements a reflective color in a visible ray region and near-infrared rays. To this end, the thickness of the first insulator layer 221 may be 10 nm to 1000 nm.

Specifically, when the thickness of the first insulator layer 221 is a visible light wavelength (800 nm or less), the gas sensor 200 may implement a reflective color in a visible light region; if the thickness of the first insulator layer 221 is too thick (if it is more than 1000 nm), there is a problem in that the clarity of the color is deteriorated, and thus the visibility is poor.

In addition, if the thickness of the first insulator layer 221 is too small (if it is 10 nm or less), it is difficult to manufacture the first insulator layer 221, and it is difficult to implement reflective colors in the visible light region, so the thickness of the first insulator layer above 221 is preferably greater than 10 nm.

It is preferable that the thickness of the first metal layer 211 is 5 nm to 50 nm. When the thickness of the first metal layer 211 is 5 nm or more, a reflective color may be implemented in a visible light region, and when the thickness of the first metal layer 211 is less than 5 nm, it is difficult to implement a clear reflective color in a visible light region.

In addition, as described above, the thickness of the first metal layer 211 may change by reacting with gas, but if the thickness of the first metal layer above 211 is less than 5 nm, there is no area where the thickness can be reduced, making it difficult to serve as a sensor.

It is preferable that the thickness of the first metal layer 211 is 50 nm or less. When the thickness of the first metal layer 211 is thicker than 50 nm, total reflection occurs with the naked eye and color is visually recognized as silver or gold, making it difficult to detect color with the naked eye.

In addition, if the thickness of the first metal layer 211 is less than 5 nm or greater than 50 nm, there is a problem in that the resonance phenomenon between the first metal layer 211 and the second metal layer 212 is reduced and color visibility is not achieved. Accordingly, the thickness of the first metal layer 211 is preferably 5 nm to 50 nm, and more preferably, the thickness of the first metal layer 211 is 5 nm to 35 nm.

It is preferable that the thickness of the second metal layer 212 is 5 nm or more. Since the second metal layer 212 can serve as a reflecting plate, it is preferable that the thickness of the second metal layer 212 is 5 nm or more for the sake thereof. More preferably, it is preferably 30 nm or more.

In the above description, the film layer 210 of the gas sensor 200 includes the first metal layer 211 and the second metal layer 212, and the optical layer 220 includes the first insulator layer 221, but is not limited thereto.

Referring to FIG. 5(b), the film layer 210 of the gas sensor 200 may further include a third metal layer 213 made of metal together with the first metal layer 211 and the second metal layer 212, and the optical layer 220 may further include a second insulator layer 222 having transparency or translucency together with the first insulator layer 221.

The second insulator layer 222 may be provided between the second metal layer 212 and the third metal layer 213, and the gas sensor 200 may have a structure of the first metal layer 211—the first insulator layer 221—the second metal layer 212—the second insulator layer 222—the third metal layer 213.

In addition, a third insulator layer-fourth metal layer may be additionally disposed under the third metal layer 213 of the gas sensor 200, and the gas sensor 200 may have a structure in which the structure of a metal layer-insulator layer-metal layer is repeated. In addition, a metal layer made of a metal may be additionally provided on the first metal layer 211.

Referring to FIG. 5(c), the gas sensor 200 may further include a catalyst layer 230 coupled to the film layer 210 to improve the reactivity of the gas. The catalyst layer 230 may be made of a material such as palladium or gold, and the catalyst layer 230 may be made of various materials as long as it can improve the reactivity of gas.

By combining the catalyst layer 230 with the film layer 210, reactivity between the film layer 210 and the gas may be improved. The catalyst layer 230 may be coupled to the film layer 210 reacting with gas, and may be coupled to the film layer 210 provided on the gas sensor 200. Referring to FIG. 5(c), the catalyst layer 230 may be coupled to the first metal layer 211.

As described above, the gas sensor 200 may have the MIM (Metal-Insulator-Metal) structure that includes a metal layer (film layer) which changes the thickness thereof by reacting with gas—an insulator layer (an optical layer) that resonates with light—a metal layer (a film layer) that reflects light.

However, the present disclosure is not limited thereto, and the gas sensor 200 may have such a structure as having an insulator layer—an insulator layer—a metal layer or an insulator layer—an insulator layer—an insulator layer.

Figure 6:
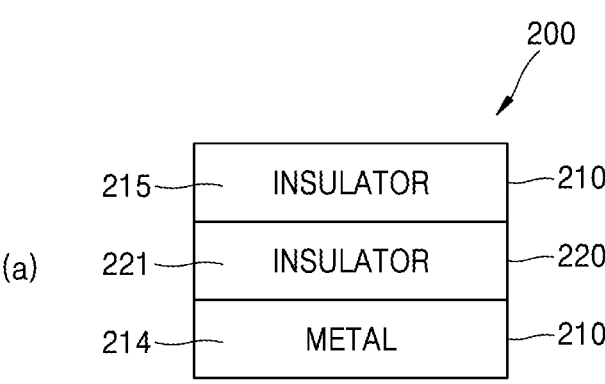
FIGS. 6(*a*) and 6(*b*) show a film layer attained from a combination of a metal layer and an insulator layer, according to an embodiment of the present disclosure.
Figure 6:
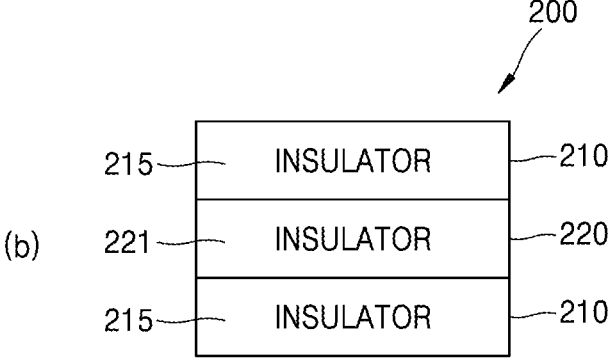

Specifically, referring to FIG. 6(a), the film layer 210 of the gas sensor 200 may include a metal layer 214 of a metal material and an insulator layer 215 having optically transparency or translucency.

The film layer 210 of the gas sensor 200 may be formed of a combination of the metal layer 214 and the insulator layer 215, and the gas sensor 200 may have such a structure as including an insulator layer 215 (a film layer 210)—an insulator layer (an optical layer 220)—a metal layer 214 (a film layer 210) as shown in FIG. 6(a).

In addition, referring to FIG. 6(b), the film layer 210 of the gas sensor 200 may include the insulator layer 215 that is optically transparent or translucent. The film layer 210 of the gas sensor 200 may be formed of the insulator layer 215, and the gas sensor 200 may have a structure of the insulator layer 215 (the film layer 210)—the insulator layer (the optical layer 220)—the insulator layer 215 (the film layer 210) as shown in FIG. 6(b).

Figure 7:
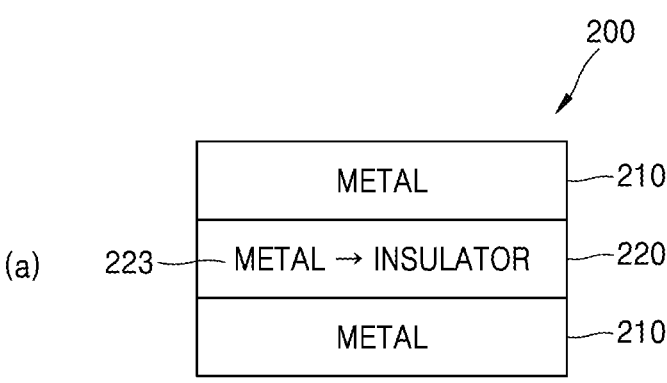
FIGS. 7(*a*) and 7(*b*) show a gas reaction metal layer having optical transparency or translucency generated by a reaction of an optical layer with gas, according to an embodiment of the present disclosure.
Figure 7:
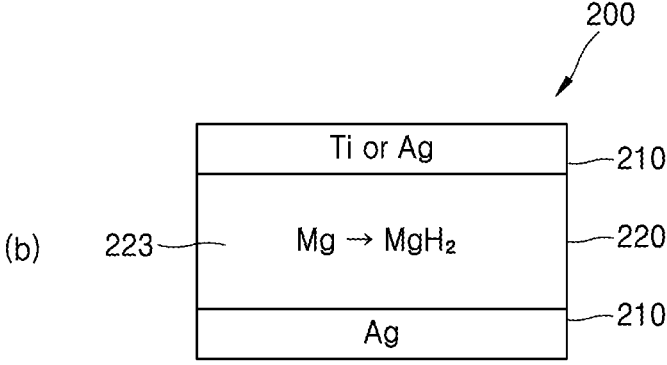

Referring to FIGS. 7(a) and 7(b), the optical layer 220 of the gas sensor 200 may be formed of a gas reaction metal layer 223 made of a metal. The gas reaction metal layer 223 may be a metal that reacts with gas to be optically transparent or translucent.

Since the gas reaction metal layer 223 reacts with gas to have transparency or translucency, the gas reaction metal layer 223 may serve as an insulator layer. Specifically, referring to FIG. 7(b), the gas reaction metal layer 223 may be formed of an Mg metal layer.

As the Mg metal layer reacts with hydrogen and changes to a layer of MgH2, it can have transparency or translucency. However, the gas reaction metal layer 223 is not limited to an Mg metal layer, and if it can react with gas to have transparency or translucency, the gas reaction metal layer above 223 may be made of various materials.

It is preferable that the thickness of the gas sensor 200 according to an embodiment of the present disclosure is 1,000 nm or less. The gas sensor 200 may reflect visible light that may be visually recognized by a user, or may reflect visible light and near-infrared light that may be measured by a camera, and most preferably reflect visible light. When the thickness of the gas sensor 200 is thicker than 1000 nm, the wavelength of light reflected by the gas sensor 200 may be transferred to an area other than visible light, and thus the thickness of the gas sensor 200 is preferably 1000 nm or less.

Figure 8:
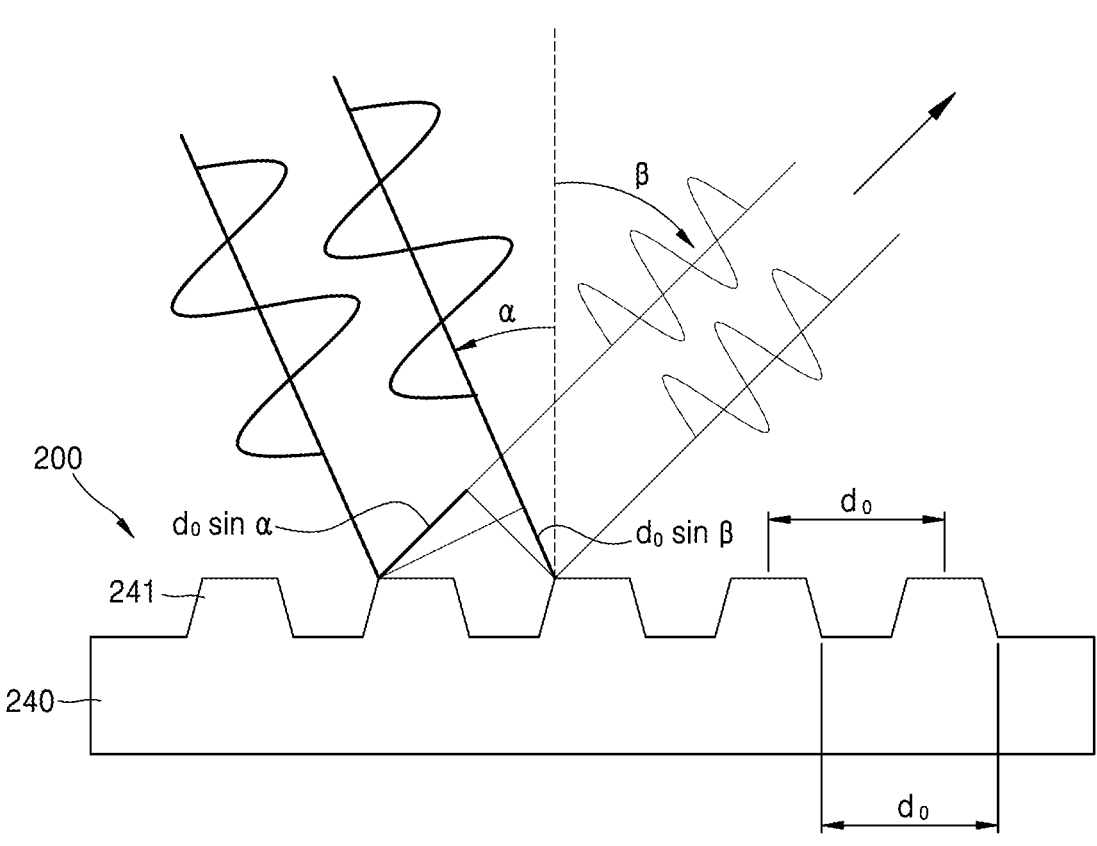
FIG. 8 shows light reflection on a gas sensor including a nano-pattern layer according to another embodiment of the present disclosure.

According to another embodiment of the present disclosure, the gas sensor 200 may include a nano-pattern layer 240 on which a pattern 241 is formed. Referring to FIG. 8, a nano-pattern 241 may be formed on the nano-pattern layer 240, and a structural color may be implemented by the nano-pattern 241.

The pattern 241 may be formed by providing a plurality of protrusions in the nano-pattern layer 240, and a width between the plurality of protrusions may be a width $d_0$ between the patterns 241.

Figure 9:
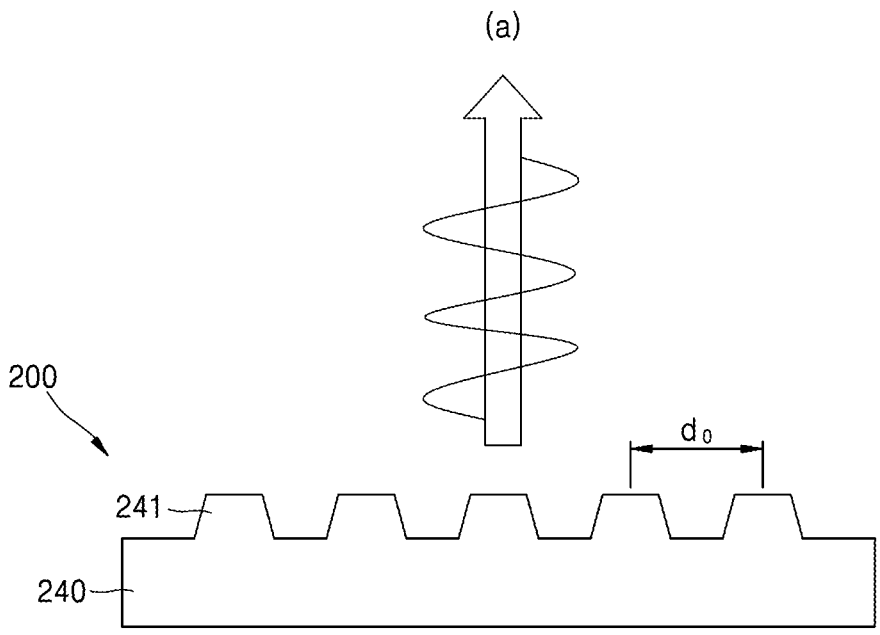
FIG. 9 shows a change of a reflectivity value of light reflected from a gas sensor as a width between patterns of a nano-pattern layer changes due to a reaction between gas and the nano-pattern layer, according to another embodiment of present disclosure.
Figure 9:
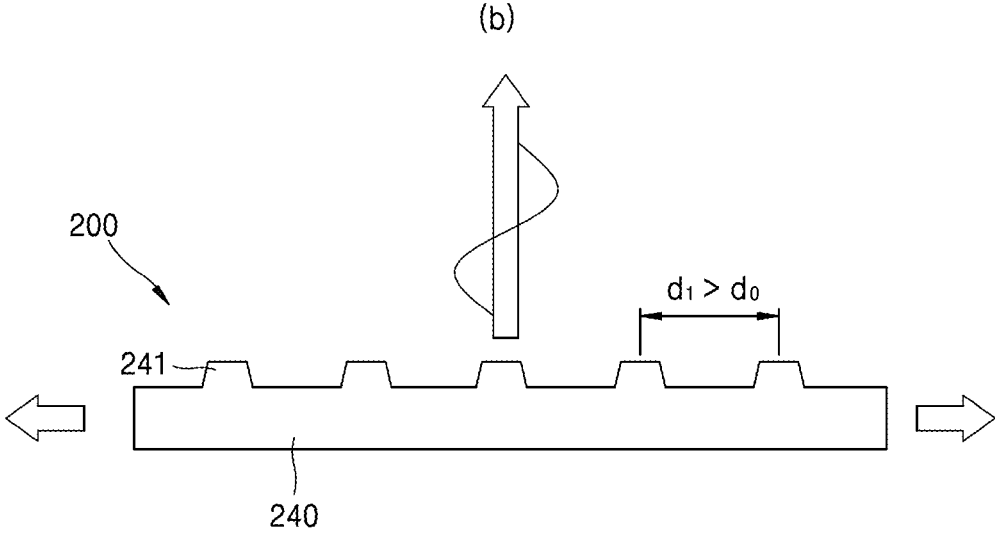

Referring to FIG. 9, the nano-pattern layer 240 may react with gas, and when the nano-pattern layer 240 reacts with gas, the width between the patterns 241 is changed ($d_0 > d_1$).

As the width between the patterns 241 changes, the reflectivity value of the wavelength of light reflected by the gas sensor 200 changes, thereby implementing a color change. The light receiver 122 of the optical measurement device 120 may detect a change in the reflectivity value, and may measure the accumulated concentration of the gas, the concentration of the gas, and the like through the change in the reflectivity value.

The method and process of measuring the cumulative concentration of gas and the concentration of gas by changing the color by the nano-pattern layer 240 of the gas sensor 200 are the same as the method and process of measuring the cumulative concentration of gas and the concentration of gas by changing the color of the gas sensor 200 including the film layer 210 and the optical layer 220, so the detailed description with respect thereto will be omitted.

According to an embodiment of the present disclosure, it is preferable that the width between the patterns 241 of the nano-pattern layer 240 may be 200 nm to 2000 nm. The governing equation for the wavelength of light reflected by the nano-pattern layer 240 may be changed according to a viewing angle facing the nano-pattern layer 240.

When the color gas sensor module including the optical measurement device according to an embodiment of the present disclosure is used, the viewing angle of the nano-pattern layer 240 (the gas sensor 200) must be greater than 20 degrees so that the user may visually recognize it with the naked eye.

When the viewing angle facing the nano-pattern layer 240 is 20 degrees, if the width between the patterns 241 is greater than 3000 nm or less than 200 nm, the light reflected from the nano-pattern layer 240 is displayed in the ultraviolet and far-infrared regions while deviating from the visible light and near-infrared regions, making it impossible to observe with the naked eye. Accordingly, the width between the patterns 241 of the nano-pattern layer 240 is preferably 200 nm to 3000 nm.

The width between the patterns 241 of the nano-pattern layer 240 according to an embodiment of the present disclosure may be one-dimensional (1 D), two-dimensional (2D), and three-dimensional (3D) width. Specifically, the width between the patterns 241 may be a one-dimensional width formed by extending in only one direction, and may be a two-dimensional width formed by extending in two directions (x, y). In addition, the width between the patterns 241 may be a three-dimensional width formed by extending in three directions (x, y, z).

The color gas sensor module including the optical measurement device according to an embodiment of the present disclosure described above may be operated as follows.

When the color gas sensor module including the optical measurement device according to an embodiment of the present disclosure is exposed to harmful gas, the harmful gas is introduced into the housing 110 through the gas movement passages 111 of the housing 110. At this time, gas other than harmful gas may be selectively removed through the membrane 112.

When harmful gas is introduced into the housing 110, the color of the gas sensor 200 changes as the harmful gas reacts with the gas sensor 200. In this way, it is possible to detect the harmful gas by checking the change in the gas sensor 200.

In addition, when harmful gas flows into the housing 110, the harmful gas reacts with the gas sensor 200, and the reflectivity value of the light reflected from the gas sensor 200 changes.

When the reflectivity value of the light reflected from the gas sensor 200 changes, the light receiver 122 of the optical measurement device 120 detects it and transmits a signal to the controller. The controller may determine the accumulated concentration of the gas, the concentration of the gas, and the like through such a signal.

According to an embodiment of the present disclosure, the controller may be connected to various mobile devices, wearable devices, and electronic devices, and the controller may transmit signals regarding the cumulative concentration of the gas, the concentration of the gas, etc. determined according to the color change of the gas sensor 200 to various mobile devices, wearable devices, and electronic devices. The mobile device, the wearable device, and the electronic device may receive a signal from the controller and display information regarding the accumulated concentration of the gas, the concentration of the gas, and the like to the outside.

In this way, the color gas sensor module including the optical measurement device according to the embodiment of the present disclosure may quantitatively display the accumulated concentration of gas, the concentration of gas, and the like while measuring the accumulated concentration of gas, the concentration of gas with low power.

The color gas sensor module including the optical measurement device according to an embodiment of the present disclosure described above has the following effects. Conventional gas sensors required a heating device, and conventional gas sensors qualitatively measured the gas concentration by naked eyes or camera images.

However, the color gas sensor module, which includes an optical measurement device according to the embodiment of this disclosure, has the advantage of removing a separate heating device by using a gas sensor and an optical measurement device that change color in response to gas.

Through this, the color gas sensor module including the optical measurement device according to the embodiment of the present disclosure has the advantage of detecting a gas with low power and expressing it in color, and can be miniaturized by using low power.

The color gas sensor module including the optical measurement device according to an embodiment of the present disclosure may be miniaturized while using low power, and thus may be installed and used in mobile devices, electronic devices, and wearable devices.

The color gas sensor module including the optical measurement device according to an embodiment of the present disclosure has the advantage of remotely measurement harmful gas concentration and gas concentration changes in the polluted area by being attached to and used in a movable electronic device such as a drone.

The color gas sensor module including the optical measurement device according to an embodiment of the present disclosure has the advantage of quantitatively displaying the concentration of the gas by detecting the color change of the gas sensor through the optical measurement device and transmitting the signal, and measuring the accumulated concentration of the gas.

The color gas sensor module including the optical measurement device according to an embodiment of the present disclosure has the advantage of improving durability by including a membrane in a housing provided with the optical measurement device and the gas sensor.

As described above, the present disclosure has been described with reference to an embodiment shown in the drawings, but this is merely exemplary, and those skilled in the art will understand that various modifications and modifications of the embodiments may be made therefrom. Therefore, the true technical protection scope of the present disclosure should be determined by the technical idea of the attached patent claims.

The invention claimed is:

1. A color gas sensor module including an optical measurement device, the color gas sensor module comprising:
   a housing having an interior space therein and a gas movement passage allowing a gas to move from outside to the interior space;
   the optical measurement device provided in the housing and including a light emitter that emits light and a light receiver that receives reflected light; and
   a gas sensor provided in the housing and configured to change color by reacting with the gas,
   wherein the light emitter emits light to the gas sensor, and the light receiver receives light reflected from the gas sensor,
   wherein the gas sensor includes a nano-pattern layer on which patterns are formed,
   wherein the patterns are separated from each other, and
   wherein the nano-pattern layer is configured such that a distance between the patterns changes when reacting with the gas.

2. The color gas sensor module of claim 1, wherein the light emitter of the optical measurement device emits light onto the gas sensor, and
   the light receiver measures a reflectivity of a wavelength of the light reflected from the gas sensor.

3. The color gas sensor module of claim 1, wherein the housing includes a plurality of gas movement passages.

4. The color gas sensor module of claim 3, wherein at least one of the plurality of gas movement passages includes a membrane capable of selectively removing a designated gas.

5. The color gas sensor module of claim 1, wherein the gas sensor includes two or more film layers and an optical layer between the film layers.

6. The color gas sensor module of claim 5, wherein the film layer of the gas sensor includes a first metal layer including a metal and a second metal layer including a metal,
   the optical layer includes a first insulator layer having transparency or translucency, and
   the first insulator layer is between the first metal layer and the second metal layer.

7. The color gas sensor module of claim 6, wherein the film layer of the gas sensor further includes a third metal layer including a metal,
   the optical layer further includes a second insulator layer having transparency or translucency, and the second insulator layer is between the second metal layer and the second metal layer.

8. The color gas sensor module of claim 6, wherein the optical layer of the gas sensor comprises a gas reaction metal layer including a metal, and the gas reaction metal layer reacts with the gas to become optically transparent or translucent.

9. The color gas sensor module of claim 5, wherein the gas sensor includes a catalyst layer that improves reactivity to gas when combined with the film layer.

10. The color gas sensor module of claim 5, wherein the film layer of the gas sensor includes an insulator layer that is optically transparent or translucent.

11. The color gas sensor module of claim 5, wherein the film layer of the gas sensor includes a metal layer including a metal material, and an insulator layer having optical transparency or translucency.

12. The color gas sensor module of claim 5, wherein a thickness of the film layer of the gas sensor changes in response to the film layer reacting with gas.

13. The color gas sensor module of claim 1, wherein the width between the patterns of the nano-pattern layer is 200 nm to 3,000 nm.

* * * * *